United States Patent [19]

Harris

[11] 4,089,335

[45] May 16, 1978

[54] MICROSYRINGE

[76] Inventor: Rano J. Harris, 1945 Carolyn Sue Dr., Baton Rouge, La. 70815

[21] Appl. No.: 740,821

[22] Filed: Nov. 11, 1976

[51] Int. Cl.$^2$ .................................................. A61M 5/00
[52] U.S. Cl. ................................. 128/218 P; 128/234
[58] Field of Search .......... 128/218 P, 218 PA, 218 C, 128/218 R, 234, 237, 215; 222/386, 390

[56] References Cited

U.S. PATENT DOCUMENTS

| 2,602,447 | 7/1952 | Kollsman | 128/218 P |
| 3,281,023 | 10/1966 | Bruck et al. | 128/218 C X |

FOREIGN PATENT DOCUMENTS

| 1,090,826 | 10/1960 | Germany | 128/218 P |
| 2,261,631 | 6/1974 | Germany | 128/218 P |

*Primary Examiner*—John D. Yasko
*Attorney, Agent, or Firm*—Llewellyn A. Proctor

[57] ABSTRACT

A microsyringe comprised of a barrel provided with an axial bore, at the forward or outlet end of which is affixed a hollow needle, and within the opposite end of which is fitted a slidable plunger. The forward terminal end of the plunger is hollow and provided with a fixed seal. The fixed seal is of cylindrical shape, and constituted of a resilient, flexible or semi-flexible material, of external diameter substantially equal to or slightly larger than the internal diameter of the bore, and includes a shank or projection of relatively smaller diameter which extends into the hollow forward portion of the plunger. The seal is held within the forward end of the plunger by inward thrust of the plunger wall, as produced by punching or crimping the wall formed within the hollow end of the plunger to force the wall inwardly against the seal projection to hold the seal firmly in place, and in proper alignment.

10 Claims, 7 Drawing Figures

MICROSYRINGE

It is known to use syringes for various purposes, particularly microsyringes now widely used for withdrawing and delivering accurately measured quantities of fluid specimens into various media, e.g., modern analytical instruments.

Typically, a microsyringe is comprised of a strong walled glass tube or barrel with a longitudinal bore of extremely small diameter, provided with a needle or cannula connected to the outlet end of the bore. The barrel is provided with indicia indicative of the volume of the bore, and a plunger or piston is slidably mounted in the end of the barrel opposite the needle. Illustrative of its use, the needle end of the syringe is typically inserted into a septum inlet of a gas chromatograph whereupon a measured quantity of the fluid contents of the bore of the syringe can be displaced by the forward movement of the plunger.

A problem associated with this type of syringe is that it is extremely difficult to effectively seal the annulus between the forward face of the plunger, and the inside wall of the barrel. If the annulus is made leakproof by use of a seal of adequately large diameter, the frictional drag of the plunger as it is moved within the bore can be quite enormous. The friction is often sufficient to dislodge the seal from the tip of the plunger, and this is particularly so with the types of seals used in microsyringes which have plungers of very small external diameter. The placement of such seals during manufacture, and their replacement after such seal has been damaged or displaced during use is indeed troublesome.

It is, accordingly, a prime object of this invention to overcome these and other disadvantages.

It is, in particular, an object of the present invention to provide a novel syringe for use in accurately dispensing small quantities of fluids, particularly one containing a novel seal associated, integral, and movable with the plunger of said syringe.

A further object is to provide a new and novel syringe, inclusive of the conventional cannula or tubular needle fitted within an end of a barrel, and slidable plunger fitted within the opposite end of the barrel, but one which contains a novel seal affixed to the forward terminal end of the plunger.

Another object is to provide such syringe, inclusive of its plunger and integral seal, which can be readily manufactured, and easily assembled for usage.

These objects and others are accomplished in accordance with the present invention which comprises the usual combination of a barrel provided with an axial opening or bore, within one end (and within the bore) of which is affixed a cannula, or hollow or tubular needle, and within the other end (and within the bore) of which is slidably mounted a piston or plunger provided with a fixed forward seal. The forward terminal end of the plunger is hollow. The forward end of the fixed seal is of cylindrical shape, and constituted of a resilient, flexible or semi-flexible material of external diameter substantially equal to or slightly larger than the internal diameter of the bore, and includes a shank or projection of relatively smaller diameter which extends into the hollow forward portion of the plunger. The seal is held within the forward end of the plunger by inward thrust of the plunger wall, as produced by punching or crimping the wall formed within the hollow end of the plunger to force the wall inwardly against the seal projection to hold the seal firmly in place, and in proper alignment.

The advantages of seals formed on plungers in this manner vis-a-vis conventional seals are manifested in several ways during manufacture, assembly, use, and disassembly for cleaning and reassembly, or replacement. The seal per se is much more easily prepared for mounting, and likewise the plunger which need only be provided with a forward opening of sufficient depth, and sized to retain the projection portion of the seal which is quite adequately secured by crimping or punching the wall to force the wall inwardly against the seal projection. The so-secured seal is quite stable and not easily dislodged or forced out of alignment by movement of the plunger. The seal itself is suitably formed of resilient, flexible or semi-rigid materials suitably elastomers or plastics such as polytetrafluoroethylene (Teflon), polyethylene, natural or synthetic rubber, silicon rubber, or the like.

These and other features and advantages will be better understood by reference to the following detailed description and to the accompanying drawings to which reference is made in the description. In the drawings, similar numbers are used to represent similar parts or components in the different figures, and subscripts are used to designate a plurality of analogous parts or components.

Referring to the drawings.

Figure 1:
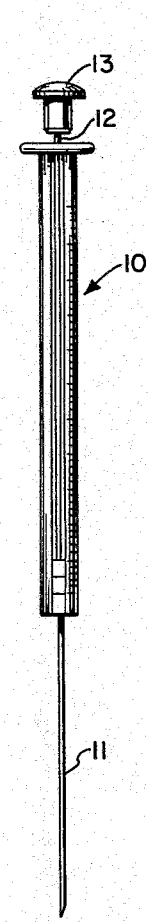
FIG. 1 is a perspective, overall view of a syringe in accordance with the present invention.
Figure 2:
FIG. 2 is a perspective view of the plunger portion of the syringe depicted by reference to the preceding figure, inclusive particularly of a seal incorporated on the forward end of the plunger.
Figure 3:
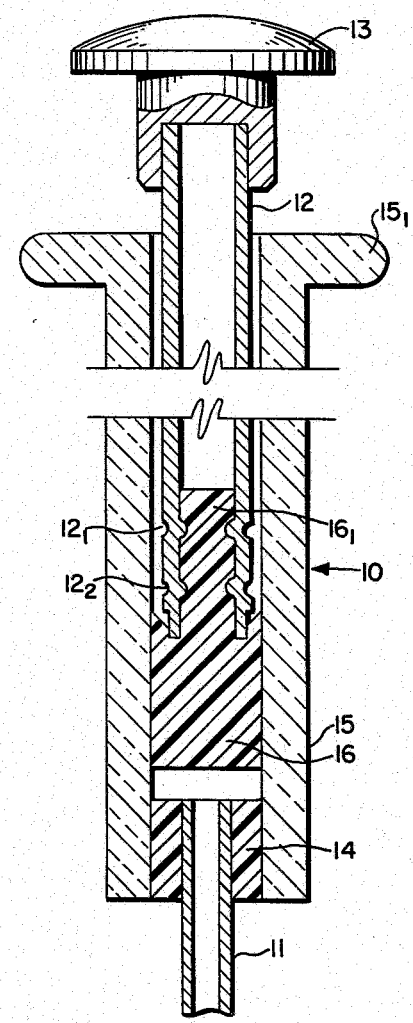
FIG. 3 is a fragmentary view, principally in cross-section, of the syringe depicted by reference to FIG. 1, showing particularly the seal located on the forward end of the plunger.

Referring first to FIGS. 1–3 of the drawings, there is depicted generally a syringe 10, inclusive of a barrel 15 within one end of which is mounted a cannula or tubular needle 11, and within the opposite end, suitably provided with a flanged portion $15_1$, there is mounted a slidable hollow plunger 12. The barrel 15 is of cylindrical, or tubular, configuration provided with an axial opening or bore, and suitably it is constituted of metal, plastic or glass suitably scribed with indicia indicative of the volume of the bore. The cannula or needle 11 is suitably affixed via an end within the forward end of the barrel 15 via means of a tubular plastic seal 14 within which it is concentrically mounted. The plunger 12, slidably mounted within the opposite end of the bore of the barrel 15, and traversable therein, is provided with a handle or thumb button 13, and the opposite end thereof is provided with a resilient, flexible, or semi-flexible seal 16.

Figure 4:
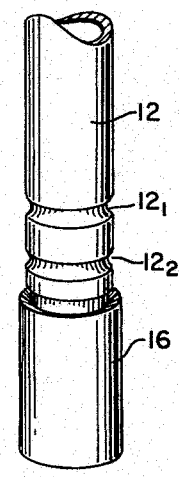
FIG. 4 is a fragmentary view, in perspective, of the lower end of the plunger, inclusive of the plunger seal, depicted by reference to the preceding figures.

The seal 16, carried on the forward end of the plunger 12, constitutes a key and novel feature of the present invention. The forward portion of the seal 16 is of external diameter substantially equal to or slightly larger than the internal diameter of the bore of the barrel 15. The seal 16 impinges circumferentially upon the wall 15 of the barrel which forms the bore to provide a tight fit which prevents leakage of fluid around or past the seal 16 into the annulus as the plunger 12 is moved within the bore. The forward end of the plunger 12 is necessarily hollow, and the seal 16 is affixed thereto via a projecting shank portion, or portion of relatively small external diameter $16_1$, which is extended into the hollow forward end of the plunger 12 and the latter crimped (as best shown by reference to FIGS. 3 and 4) to hold the seal 16 in place upon the forward end of the plunger 12.

In general, the shank $16_1$ of seal 16 approximates, or is of equal or greater length than the larger diameter portion of the seal 16. With the shank $16_1$ of the seal 16 in place within the hollow forward end of the plunger 12, generally a plurality of spaced apart circumferential, or ring-like grooves $12_1, 12_2$ are pressed into the forward end of the plunger 12 as via the use of a crimping tool to hold the seal 16 tightly in place. A seal 16 formed on the forward end of the plunger in this manner, tightly fitted within the bore to form an effective leak-proof member, has been found to provide excellent stability, even when the inside diameter of the bore through barrel 15 is 0.062 inch, and smaller. Seals so formed have, in fact, been found admirably suitable in bores ranging in sizes from about 0.018 inch to about 0.062 inch diameter. Preferably, in the formation of such seals the diameter of the shank portion $16_1$ of the seal 16 ranges from about 10 to about 75 percent, preferably from 30 to about 50 percent of the diameter of the large diameter portion of seal 16. Preferably, also, the grooves $12_1, 12_2$ range in depth from about 10 to about 75 percent, preferably from about 30 to about 50 percent of the diameter of the shank portion $16_1$. Seals formed in such manner, unlike prior art seals wherein seals were provided with an opening and fitted upon a projection located on the end of a plunger, are extremely stable, and adhere tenaceously to the forward end of the hollow plunger on which they are fitted. Seals so formed are suitable for use in plastic, metal, glass, inclusive particularly of precision bore glass, and the like.

Figure 5:
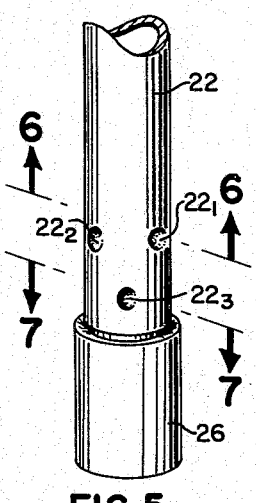
FIG. 5 is a fragmentary view, in perspective, of the lower or forward end of a second plunger of type suitable for use in the syringe embodied in FIG. 1, inclusive of plunger seal.
Figure 6:
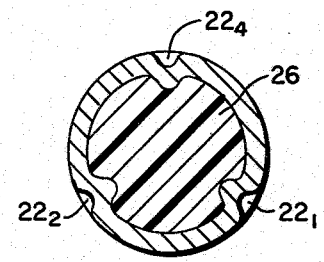
FIG. 6 is a cross-sectional view of the plunger taken along line 6—6 of FIG. 5.
Figure 7:
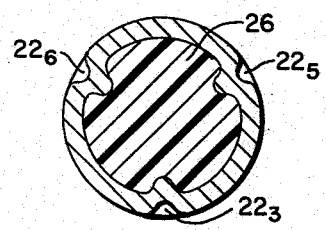
FIG. 7 is a cross-sectional view of the plunger taken along line 7—7 of FIG. 5.

In another embodiment, as shown by reference to FIGS. 5-7, a seal 26, constructed in a manner similar to seal 16, can be affixed upon the forward end of a hollow plunger 22 by the use of a plurality of indentations $22_1, 22_2, 22_3, 22_4, 22_5, 22_6$ placed in the forward end of said plunger 22 as via use of a center punch after the shank portion of said seal 26 has been inserted in place into the hollow opening, the entry portion of which is located in the face of the face of the plunger 22. In such embodiment, suitably, a plurality of rows of the punch marks, or indentations, can be made, i.e., as represented by the row of punch marks $22_1, 22_2, 22_4$ (FIG. 6) and the row of punch marks $22_3, 22_5, 22_6$ (FIG. 7); or the indentations can be arrayed in random distribution from the front to the leading edges of the several effective areas of possible attachment lying at the interface between the inside wall of the plunger 22 and the external face of the seal 26. The depth of the punch marks corresponds with the depth of the circumferential grooves $12_1, 12_2$ described principally by reference to FIGS. 3 and 4.

The barrel of the syringe can be made of substantially any material, metal alloys, steel, iron, or the like. Preferably, however, it is constructed of plastic or glass. The needle and plunger can be composed of stainless steel, tungsten, chrome, platinum alloy, or the like. Seals can be made of generally conventional materials, including rubber, neoprene, nylon, and the like but preferably is a self-lubricating type of packing. Polytetrafluoroethylene, such as Teflon (Dupont Trademark for polytetrafluoroethylene), is a highly preferred material and has been found to provide excellent results.

It is apparent that various substitutions, modifications and changes can be made in, e.g., as in the location, the precise construction materials, or in the absolute size, shape and relative dimensions of the parts, without departing the spirit and scope of the invention. It is also feasible, e.g., to change the size and shape, or location, as well as the number of the recesses, slots, grooves, or indentations used to hold the seal within the forward end of the hollow plunger.

Having described the invention, what is claimed is:

1. A microsyringe for use in the withdrawal and delivery of accurately measured quantities of a fluid specimen which comprises a barrel provided with an axial bore, a hollow needle affixed to the forward outlet end of the barrel, a plunger slidably mounted in the bore at the opposite end of the barrel, the forward end of said plunger being hollow and provided with a fixed seal of cylindrical shape constituted in part of a resilient material of external diameter substantially equal to the internal diameter of the bore which ranges up to about 0.062 inch, and in part of a shank of relatively smaller diameter of equal or greater length than the external diameter of the larger diameter portion of said seal which is extended into the hollow forward portion of the plunger, fitted tightly over its entire length, and retained therein by an inward thrust of the wall of the plunger which pinches against the shank to hold the seal firmly in place, and in proper alignment.

2. The apparatus of claim 1 wherein the shank portion of the seal ranges from about 10 to about 75 percent of the diameter of the large diameter portion of the seal, the inward thrust of the wall is formed by a plurality of circumferential grooves, and the grooves range in depth from about 10 to about 75 percent of the diameter of the shank portion of the seal.

3. The apparatus of claim 2 wherein the inward thrust of the wall is formed by two spaced-apart circumferential grooves.

4. The apparatus of claim 2 wherein the inward thrust of the wall is formed by a plurality of punch marks.

5. The apparatus of claim 4 wherein the punch marks are arrayed in a plurality of spaced-apart rows.

6. The apparatus of claim 5 wherein the punch marks are arrayed in two spaced-apart rows.

7. The apparatus of claim 1 wherein the seal is constituted of Teflon.

8. The apparatus of claim 1 wherein the plunger is of external diameter ranging up to about 0.062 inch, the external diameter of the large diameter portion of the seal is of diameter equal to that of the plunger, and the shank portion of the seal ranges from about 10 to about 75 percent of the large diameter portion of the seal.

9. The apparatus of claim 8 wherein the plunger is of external diameter ranging from about 0.018 inch to about 0.062 inch diameter.

10. The apparatus of claim 9 wherein the seal is retained within the plunger by a plurality of circumferential grooves, the depth of which ranges from about 10 to about 75 percent of the small diameter portion of the seal.

* * * * *